(12) United States Patent
Muhl et al.

(10) Patent No.: US 7,652,490 B2
(45) Date of Patent: Jan. 26, 2010

(54) MEASURING DEVICE FOR MEASURING THE STATE OF OILS OR FATS

(75) Inventors: Mike Muhl, Freiburg (DE); Juergen Hall, Friedenweiler (DE)

(73) Assignee: Testo AG, Lenzkirch (DE)

( * ) Notice: Subject to any disclaimer, the term of this patent is extended or adjusted under 35 U.S.C. 154(b) by 180 days.

(21) Appl. No.: 11/547,761

(22) PCT Filed: Mar. 30, 2005

(86) PCT No.: PCT/EP2005/003322

§ 371 (c)(1),
(2), (4) Date: Oct. 11, 2007

(87) PCT Pub. No.: WO2005/098419

PCT Pub. Date: Oct. 20, 2005

(65) Prior Publication Data

US 2008/0186033 A1      Aug. 7, 2008

(30) Foreign Application Priority Data

Apr. 6, 2004 (DE) ........................ 10 2004 016 957

(51) Int. Cl.
*G01R 27/08* (2006.01)

(52) U.S. Cl. ........................ 324/691; 324/694; 324/698

(58) Field of Classification Search ............... 324/691, 324/694, 698
See application file for complete search history.

(56) References Cited

U.S. PATENT DOCUMENTS 3,739,265 A * 6/1973 Skildum ..................... 324/673

(Continued)

FOREIGN PATENT DOCUMENTS

DE            35 07 990 A1      9/1985

(Continued)

OTHER PUBLICATIONS

U. Demisch, M. Muhl: "Electronic nose for detection of the deterioration of frying fat-comparative studies for a new quick test", 3rd International Symposium on Deep Fat Frying, Mar. 20, 2000, Seiten 11-12, XP002330509, Hagen, Seite 11.

(Continued)

*Primary Examiner*—Timothy J Dole
*Assistant Examiner*—Farhana Hoque
(74) *Attorney, Agent, or Firm*—Muirhead and Saturnelli, LLC

(57) ABSTRACT

A measuring device is used to measure the state of a liquid product which is to be measured, in particular oil or fat. Said measuring device comprises a housing, a hollow connecting element which is secured therein and a carrier which is applied to the opposite end of the connecting element, said carrier being used to receive a sensor which can be used to measure the electric property of a product which is to be measured. The sensor is in contact with the measuring unit by means of at least one electric line, which is arranged in the region of the housing and/or with the end of the connecting element oriented towards the housing. The measuring device comprises means which can be used to minimize the falsifying effect of the water content in the product, which is to be measured, on the measuring result.

19 Claims, 5 Drawing Sheets

U.S. PATENT DOCUMENTS

| | | | |
|---|---|---|---|
| 3,746,974 A | | 7/1973 | Stoakes et al. |
| 4,082,997 A | | 4/1978 | Ohtsu et al. |
| 5,592,098 A | * | 1/1997 | Suzuki et al. ............... 324/663 |
| 5,818,731 A | | 10/1998 | Mittal et al. |
| 5,824,889 A | * | 10/1998 | Park et al. ................ 73/114.55 |
| 6,282,947 B1 | | 9/2001 | Schön et al. |
| 6,469,521 B1 | | 10/2002 | Klün et al. |
| 2003/0155935 A1 | | 8/2003 | Klun et al. |
| 2004/0060344 A1 | | 4/2004 | Kauffman et al. |

FOREIGN PATENT DOCUMENTS

| | | |
|---|---|---|
| DE | 199 47 669 A1 | 5/2001 |
| DE | 101 63 760 A1 | 7/2003 |
| EP | 1 046 908 A2 | 10/2000 |
| WO | WO98/50790 A1 | 11/1998 |

OTHER PUBLICATIONS

Irion E et al.: "Oil-Quality Prediction and Oil-Level Detection with the Temic QLT-Sensor Leads to Variable Maintenance Intervals" SAE Technical Paper Series, Society of Automotive Engineers, Warrendale, PA, US, Nr. 970847, 1997, Seiten 105-110, XP002968686, ISSN: 0148-7191, Seite 105, Spalte 2.

* cited by examiner

MEASURING DEVICE FOR MEASURING THE STATE OF OILS OR FATS

TECHNICAL FIELD

The present application relates to a measuring device for measuring the state of oils or fats.

BACKGROUND OF THE INVENTION

Hot oils or fats are often used not only once, but are utilized in deep fryers over a longer period for successively preparing different foods. The oil or fat is decomposed by oxidation at the hot operating temperatures between approximately 120° C. and 180° C. and undesirable chemical products such as free fatty acids and polymers are formed, which not only impair the taste, but may also have adverse health effects.

In order to avoid replacing frying oils or fats too early or too late, measuring devices are used for measuring the state of oils or fats, including tests for their electrical properties. Measuring the dielectric constant, which is a reliable measure of the degree of decomposition of fats or oils, is particularly suitable.

EP 1 046 908 A2, for example, describes a measuring device for measuring the state of an oil or fat, which has a housing which contains the electronic analyzer units and a data display, as well as a tubular connecting element with a sensor situated at its tip which may be directly immersed into the hot oil or fat and is suitable for determining the dielectric constant. The sensor and the electronic analyzer circuit are electrically connected via a cable laid freely within the connecting element.

DE 101 63 760 A1 describes a refinement of the above-mentioned measuring device. In the measuring device presented therein, the electrical conductors between the sensor and the electronic analyzer circuit are formed by metallic conductors printed on a ceramic substrate. The tubular connecting element is shaped in such a way that it surrounds most of the substrate and narrows downward in such a way that only the area of the substrate on which the sensor is situated is accessible from the outside. An insulating sealing adhesive is introduced and cured between the substrate and the connecting element, so that there is no electrical connection between the connecting element and the electrical conductors. In addition, a temperature-stable seal is achieved, which prevents the oil from penetrating inside the connecting element. A temperature sensor may also be provided, whose measurement results may also be processed by the electronic analyzer circuit.

The disadvantage of this measuring device is that the measured values are often greater than the actual values despite the use of reliable sensors and suitable electronic analyzer circuits.

Accordingly, it is desirable to provide a measuring device that would deliver more accurate and more reliable measurement results.

SUMMARY OF THE INVENTION

The present invention is based on the finding that during frying large amounts of water are expelled from the fried items, part of which temporarily remains in the frying oil. Since the dielectric constant of water is approximately 20 times greater than that of the frying oil, even small amounts of water result in high measured values. Depending on the age and temperature of the oil, it may take between 5 minutes (fresh oil and high temperature) and 30 minutes (old oil and low temperature) until the influence of the water has dropped to a tolerable value and the measured value coincides with the actual value of the oil.

According to the present invention, the measuring device has means which are suitable for minimizing the distorting influence of the water content in the oil or fat to be measured on the measurement result, making the measurement result considerably more accurate.

The means preferably include a moisture sensor, which is situated in the area of the measuring device to be immersed. It is thus reliably determined whether the oil contains even small amounts of water.

In another embodiment, the means include an electronic circuit for determining the complex impedance and the phase angle of the dielectric constant, providing information which essentially correlates with the water content of the oil. This allows the distorting influence due to water to be distinguished from the influence due to ageing of the oil using a single sensor.

In a further embodiment, the means have a device for filtering the oil or fat to be measured, which surrounds the sensor substrate for determining the dielectric constant. Such a device ensures that only oil from which the residual moisture has been removed by the drying filter device reaches the sensor.

The measuring device advantageously also has a temperature sensor which provides additional information for making the determination of the state of the oil or fat to be measured more accurate.

Further properties, features, and advantages of the present invention are derived from the description that follows and the appended drawing.

BRIEF DESCRIPTION OF THE DRAWINGS

Embodiments of the system are described with reference to the several figures of the drawings, in which.

DETAILED DESCRIPTION OF VARIOUS EMBODIMENTS

Referring now to the figures of the drawings, the figures comprise part of this specification and illustrate exemplary embodiments of the described system. It is to be understood that in some instances various aspects of the system may be shown schematically or may be exaggerated or altered to facilitate an understanding of the system.

Figure 1:
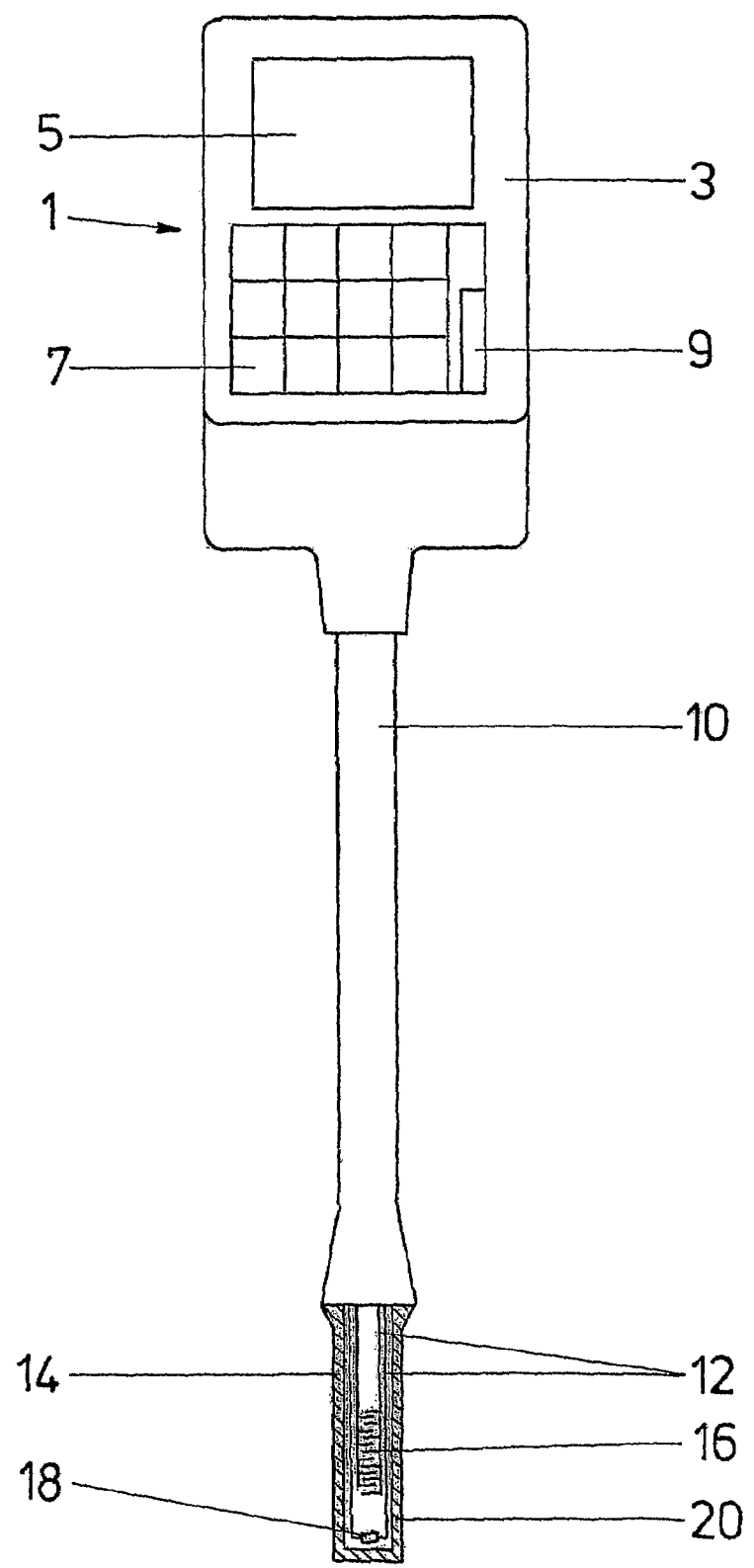
FIG. 1 shows a measuring device according to an embodiment of the present invention in a front view.

FIG. 1 shows a measuring device 1 according to the present invention for measuring the state of oils or fats, which has a housing 3 in its upper area. The housing has a display 5 for displaying measured values. The display is preferably designed as an LCD display and is switchable between graphic display, e.g., color coding of the measured values, and numerical display. A keyboard 7 is provided for inputting control instructions, via which instructions may be issued to the central control unit (not shown). Keyboard 7 is preferably designed as a membrane keyboard. The housing may preferably also have an interface 9, which may be used for communication with external computers. Measuring device 1 is preferably designed to be self-adjusting. During the use of measuring device 1, housing 3 is simultaneously used as a handle for the operator.

A hollow connecting element 10, which is sufficiently long and is made of a material with poor thermal conductivity, protrudes downward from housing 3, so that the sensitive electronic analyzer circuit (not shown) of measuring device 1, which is situated in the area of housing 3 and/or in the area of connecting element 10 facing housing 3, is adequately protected against the heat of the oil or fat to be measured. These measures ensure that the operator is able to safely perform the measurements. Connecting element 10 is preferably made of stainless steel, which, in addition to its poor thermal conductivity, is also suitable because of its unrestricted applicability in the food industry. Connecting element 10 is preferably designed as a tubular component and is suitable for receiving electrical conductors 12 running inside connecting element 10. Electrical conductors 12 are situated on at least one flat substrate 14 which is characterized by its electrical insulating properties, for example, on a substrate 14 made of a ceramic material.

In the lower area of first substrate 14, there is a sensor 16 for measuring electrical properties of the oil or fat and, preferably, a temperature sensor 18, whose measured values are conducted via electrical conductors 12 on substrate 14 to the electronic analyzer circuit. A protective means 20 for protecting sensors 16, 18 against external influences, in particular against contact with the bottom or the walls of the measuring container, may be applied to the lower area of substrate 14. In the present case, protective means 20 is designed as a peripheral edge of flat substrate 14, connected to connecting element 10.

The gap between substrate 14 and connecting element 10 is insulatingly sealed via suitable sealants (not shown). In the lower end area of connecting element 10, a suitable adhesive, for example, a silicone adhesive, is injected into the gap between substrate 14 and connecting element 10, so that these are not in direct contact and thus are insulated from one another. At the same time, the adhesive functions as a seal of connecting element 10, so that no oil or fat is able to penetrate into the inside of connecting element 10. The adhesive surface must reliably prevent water inclusions; otherwise an explosion risk, as well as contamination of the oil or fat to be measured, may result. Substrate 14 as a single-piece element may extend to the electronic analyzer circuit; it may, however, also be isolated by placing a plurality of substrate sections together in a row via suitable conductive connecting means. This arrangement provides special advantages regarding the heat load on the electronic analyzer circuit.

Figure 2:
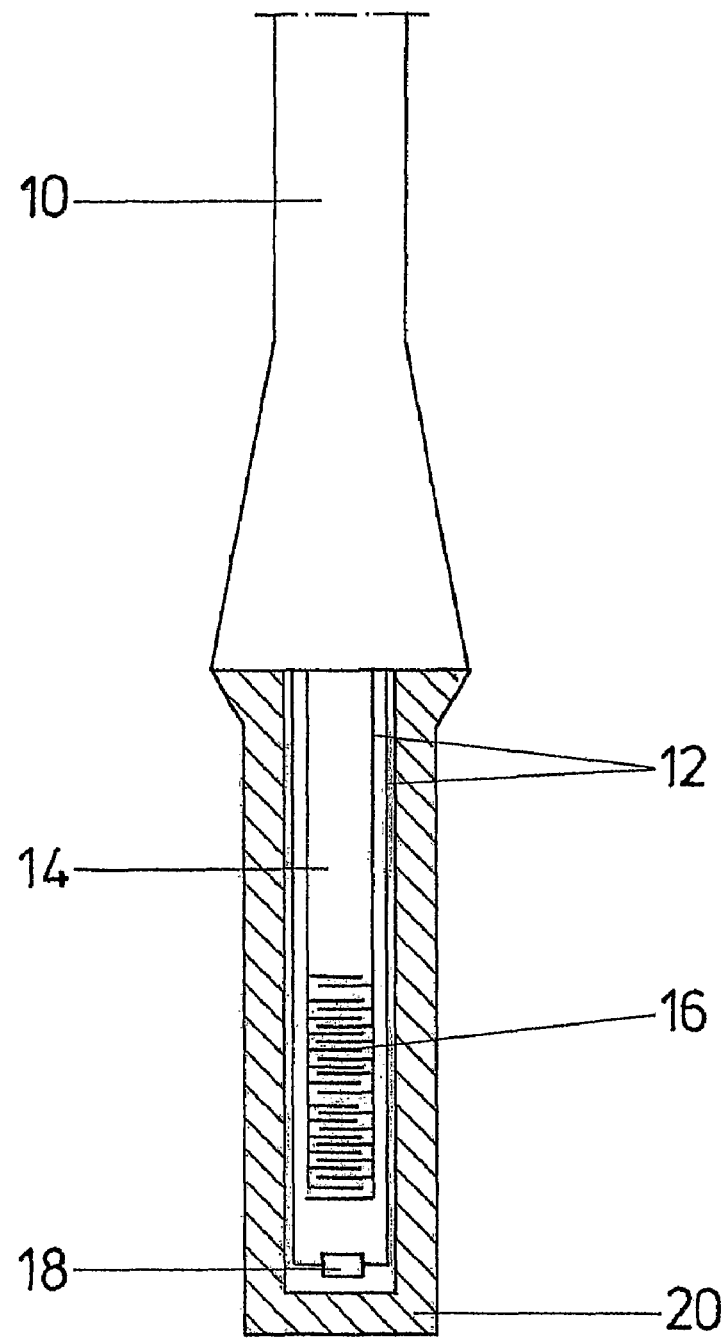
FIG. 2 shows an enlarged front view of the lower area, to be immersed, of the measuring device of FIG. 1.

FIG. 2 shows an enlarged view of the lower sections of connecting element 10 and of substrate 14, which are suitable for being immersed into the liquid to be measured. Sensor 16 for measuring the dielectric constant has a capacitor which measures the dielectric constant of the oil. It is preferably designed as an interdigital capacitor which has fine intermeshing metal conductors, each of which continues as an electrical conductor 12 leading to the electronic analyzer circuit. Conductors 12 may be made of a fine plating of gold or copper on substrate 14, the plating being printed directly onto the ceramic component. A multilayer construction of substrate 14 is also conceivable, which may better protect conductors 12 against environmental influences.

Temperature sensor 18 is designed, for example, as an electrical resistor, which may be made of platinum, for example, or another suitable material. Temperature sensor 18 may also be situated on the opposite side of substrate 14 in the area of the tip of substrate 14, which makes it possible to further reduce the size of the measuring device, while exposing both sensors 16, 18 to the same ambient temperature.

Figure 3:
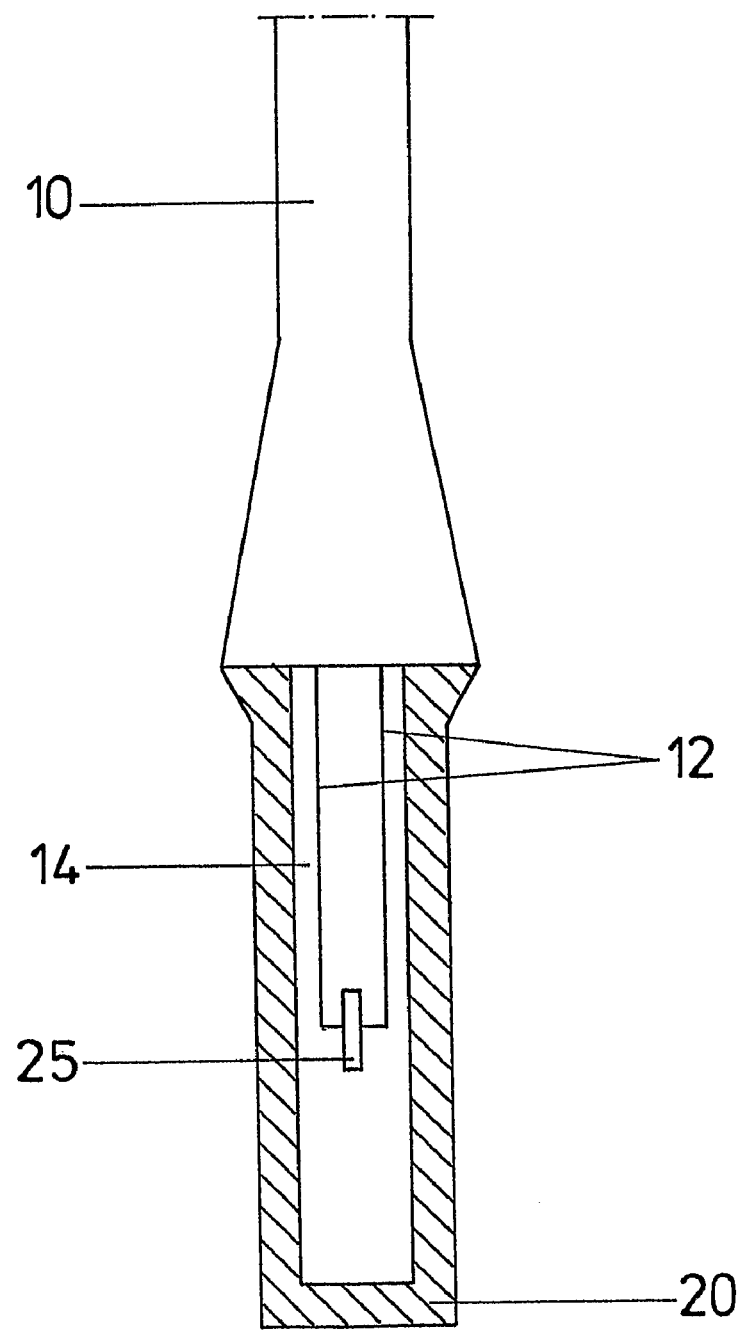
FIG. 3 shows an enlarged rear view of the lower area, to be immersed, of the measuring device of FIG. 1.

As is apparent from FIG. 3, a moisture sensor 25 for measuring the residual moisture in the oil is situated on the back side of substrate 14. Moisture sensor 25 is also connected to the electronic analyzer circuit via conductors 12; the electronic analyzer circuit uses the signals delivered by moisture sensor 25 for correcting the measured values of sensor 16. A polymer sensor is preferably used as moisture sensor 25. The entire lower area of measuring device 1 may be surrounded by a tubular sleeve (not shown) in this arrangement. It is also conceivable to position moisture sensor 25 in the area to be immersed outside connecting element 10.

Figure 4:
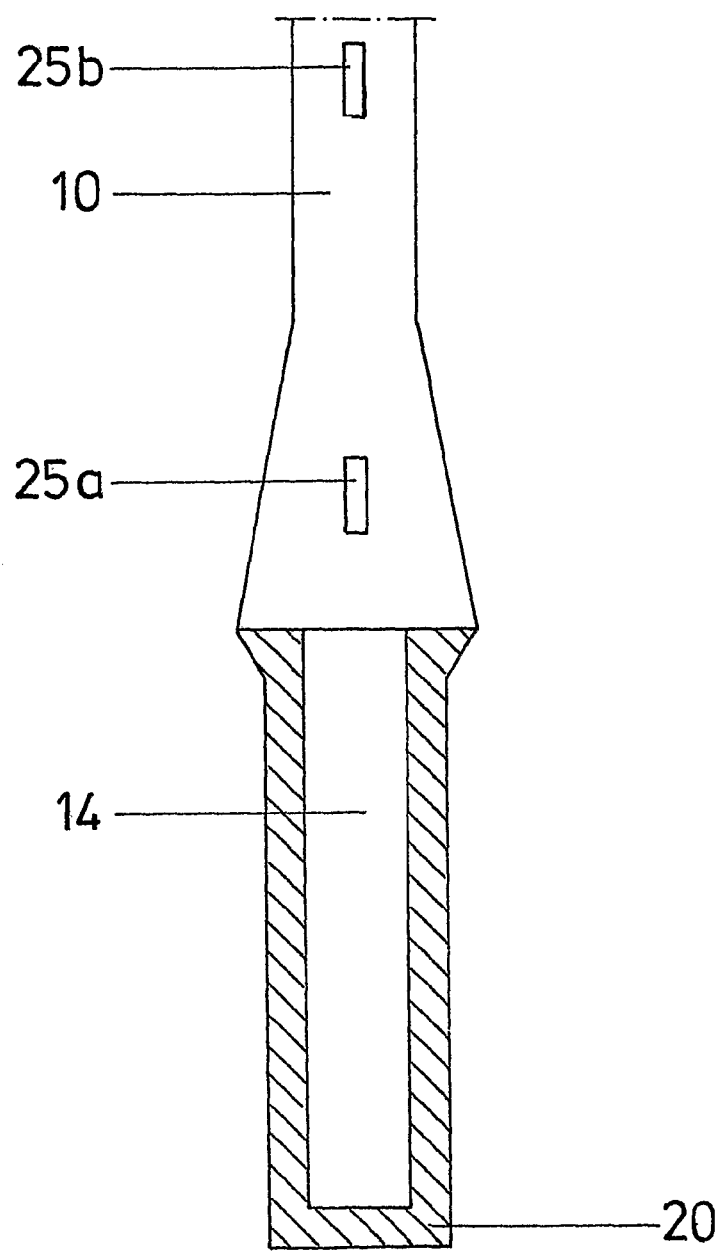
FIG. 4 shows an enlarged rear view of a variant of the lower area, to be immersed, of the measuring device of FIG. 1.

In the specific embodiment shown in FIG. 4, two moisture sensors 25a, 25b are applied to connecting element 10, lower moisture sensor 25a being positioned near the surface of the oil or fat to be measured and registering the moisture rising therefrom, while upper moisture sensor 25b is situated at a greater distance from the surface of the oil or fat to be measured. Here it measures the ambient moisture, and the difference between the measured values of the two sensors 25a and 25b is a measure of the water content in the oil or fat to be measured.

Figure 5:
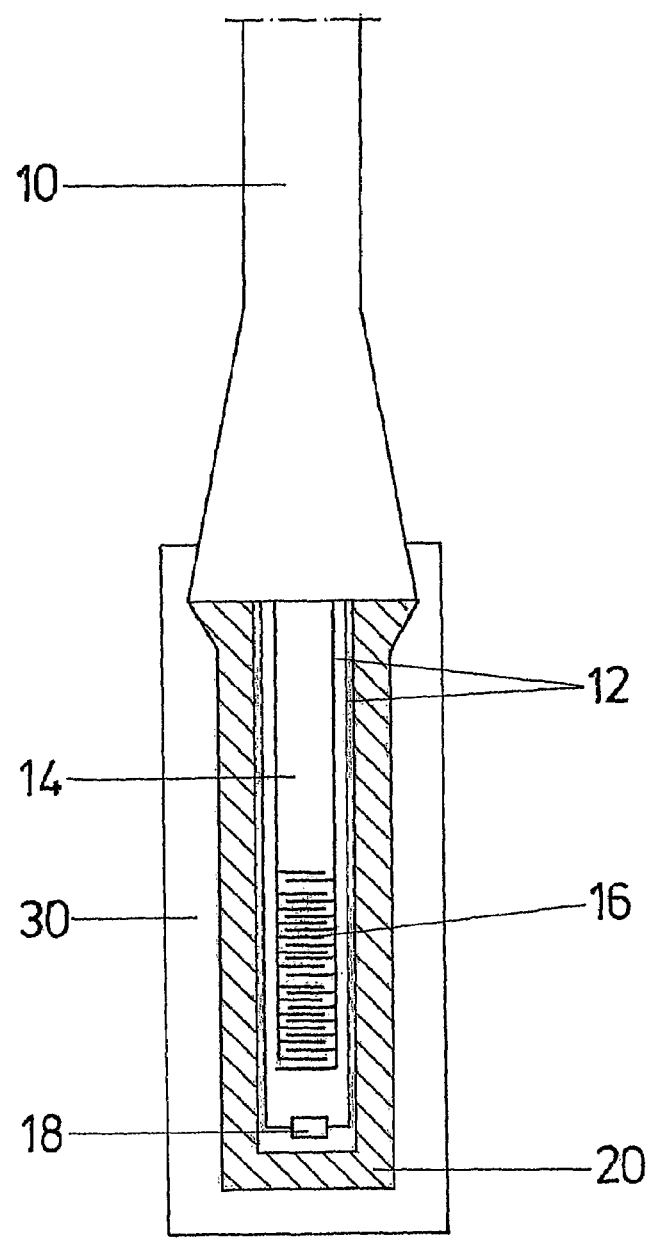
FIG. 5 shows an enlarged front view of the lower area, to be immersed, of a variant of the measuring device.

As an alternative, as FIG. 5 shows, a filtering device 30 for filtering the water content out of the oil or fat to be measured may be situated around the lower area, to be immersed, of measuring device 1. An oil-permeable water-retaining filter, which is preferably designed as a replaceable attachment, is suitable for this purpose.

It is also possible to determine the complex impedance and the phase angle of the dielectric constant using an essentially known electronic circuit. This provides information which essentially correlates with the water content of the oil, making it possible to make a distinction between the distorting influence due to water and the influence due to ageing of the oil.

The measuring device according to the present invention may also have means for compensating the measuring errors in the measuring signal and/or a display device which provides an appropriate visual and/or acoustic signal in the event of increased water content.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A measuring device for measuring the state of oils or fats, comprising:
    a housing;
    a hollow connecting element attached to the housing;
    a substrate mounted on an opposite end of the connecting element for receiving a sensor for measuring an electrical property of oil or fat to be measured, the sensor being connected to an electronic analyzer circuit via at least one electrical conductor, the electronic analyzer circuit being situated in an area of at least one of the housing and an end of the connecting element facing the housing; and
    means for minimizing a distorting influence of water content in the oil or fat to be measured on a measurement result, wherein the means for minimizing the distorting influence of the water content includes at least one moisture sensor.

2. The measuring device as recited in claim 1, wherein the means for minimizing the distorting influence of the water content includes two moisture sensors, one of which is positioned near the surface of the oil or fat to be measured and is not immersed in the oil or fat and the other one is situated near the housing for measuring the ambient moisture.

3. The measuring device as recited in claim 1, wherein the at least one moisture sensor is a polymer-based sensor.

4. The measuring device as recited in claim 1, wherein the means for minimizing the distorting influence of the water content includes at least one electronic circuit for determining a complex impedance and a phase angle of a dielectric constant.

5. The measuring device as recited in claim 1, wherein the means for minimizing the distorting influence of the water content includes a device surrounding the substrate of the sensor for filtering the oil or fat to be measured.

6. The measuring device as in claim 1 further comprising: a temperature sensor.

7. The measuring device as recited in claim 1, wherein the oil or fat is a frying oil or frying fat.

8. The measuring device as recited in claim 1, wherein the means for minimizing the distorting influence of the water content analyzes a drift in the measurement result.

9. The measuring device as recited in claim 1, wherein the means for minimizing the distorting influence of the water content includes means for compensating for measurement error in a measuring signal.

10. The measuring device as recited in claim 1, wherein the means for minimizing the distorting influence of the water content includes a display device which provides an appropriate visual or acoustic signal in the event of an increased water content.

11. The measuring device as recited in claim 1, wherein the means for minimizing the distorting influence of the water content includes:
   at least one moisture sensor;
   means for compensating measurement error in a measuring signal from the sensor;
   at least one electronic circuit for determining a complex impedance and a phase angle of the measuring signal; and
   a display device which provides an appropriate visual or acoustic signal in the event of an increased water content.

12. A measuring device measuring the state of oils or fats, comprising:
   a housing;
   a hollow connecting element attached to the housing;
   a substrate mounted on an opposite end of the connecting element for receiving a sensor for measuring an electrical property of oil or fat to be measured, the sensor being connected to an electronic analyzer circuit via at least one electrical conductor, the electronic analyzer circuit being situated in an area of at least one of the housing and an end of the connecting element facing the housing; and
   means for minimizing a distorting influence of water content in the oil or fat to be measured on a measurement result, wherein a signal from the sensor is evaluated with the aid of an electronic circuit, both an electrical property of the oil and the water content in the oil being detected by separating a complex impedance of the signal into real and imaginary portions.

13. A measuring device for measuring the state of oils or fats, comprising:
   a housing;
   at least one sensor for measuring a property of oil or fat to be measured, wherein the at least one sensor outputs a measurement signal;
   a device for addressing a distorting influence of water content in the oil or fat to be measured on the measurement signal, wherein the device outputs a correction signal; and
   an analyzer circuit coupled to the sensor and the device for addressing a distorting influence of the water content in the oil or fat, the analyzer circuit being disposed in an area of the housing, wherein the analyzer circuit adjusts the measurement signal from the at least one sensor based on the correction signal from the device for addressing the distorting influence of the water content in the oil or fat.

14. The measuring device as recited in claim 13, wherein the device for addressing the distorting influence of the water content in the oil or fat includes a moisture sensor.

15. The measuring device as recited in claim 13, wherein the at least one sensor includes a sensor for measuring electrical properties of the oil or fat.

16. The measuring device as recited in claim 13, wherein the at least one sensor includes a temperature sensor.

17. The measuring device as recited in claim 13, wherein the at least one sensor includes two sensors: a sensor for measuring electrical properties of the oil or fat and a temperature sensor.

18. The measuring device as recited in claim 13, further comprising:
   a display attached to the housing and coupled to the analyzer circuit.

19. The measuring device as recited in claim 13, wherein the analyzer circuit determines a complex impedance and a phase angle of measurement signal.

* * * * *

UNITED STATES PATENT AND TRADEMARK OFFICE
CERTIFICATE OF CORRECTION

PATENT NO. : 7,652,490 B2
APPLICATION NO. : 11/547761
DATED : January 26, 2010
INVENTOR(S) : Muhl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 292 days.

Signed and Sealed this

Twenty-third Day of November, 2010

David J. Kappos
*Director of the United States Patent and Trademark Office*